United States Patent
Shachar et al.

(10) Patent No.: US 9,655,539 B2
(45) Date of Patent: May 23, 2017

(54) SYSTEM AND METHOD FOR TARGETING CATHETER ELECTRODES

(75) Inventors: Yehoshua Shachar, Santa Monica, CA (US); Bruce Marx, Ojai, CA (US); David Johnson, West Hollywood, CA (US); Leslie Farkas, Ojai, CA (US); Steven Kim, New York, NY (US)

(73) Assignee: Magnetecs, Inc., Inglewood, CA (US)

( * ) Notice: Subject to any disclaimer, the term of this patent is extended or adjusted under 35 U.S.C. 154(b) by 1218 days.

(21) Appl. No.: 13/450,831

(22) Filed: Apr. 19, 2012

(65) Prior Publication Data

US 2012/0296200 A1 Nov. 22, 2012

Related U.S. Application Data

(63) Continuation of application No. 12/615,176, filed on Nov. 9, 2009, now abandoned.

(51) Int. Cl.
| | | |
|---|---|---|
| *A61M 25/095* | (2006.01) | |
| *A61B 5/042* | (2006.01) | |
| *A61B 34/00* | (2016.01) | |
| *A61B 18/14* | (2006.01) | |
| *A61B 18/00* | (2006.01) | |

(52) U.S. Cl.
CPC .............. *A61B 5/042* (2013.01); *A61B 34/70* (2016.02); *A61B 34/73* (2016.02); *A61B 18/1492* (2013.01); *A61B 2018/00577* (2013.01); *A61B 2018/00839* (2013.01); *A61B 2562/0209* (2013.01); *A61B 2562/043* (2013.01)

(58) Field of Classification Search
CPC ............... A61B 5/042; A61B 18/1492; A61B 34/70–34/77; A61B 2018/00577
See application file for complete search history.

(56) References Cited

U.S. PATENT DOCUMENTS

| | | |
|---|---|---|
| 3,043,309 A | 9/1959 | McCarthy |
| 3,358,676 A | 12/1967 | Frei et al. |
| 3,622,869 A | 11/1971 | Golay |
| 3,628,527 A | 12/1971 | West |

(Continued)

FOREIGN PATENT DOCUMENTS

| | | |
|---|---|---|
| DE | 102005045073 A1 | 3/2007 |
| EP | 0 147 082 A2 | 7/1985 |

(Continued)

OTHER PUBLICATIONS

Ernst et al, Initial Experience With Remote Catheter Ablation Using a Novel Magnetic Navigation System Magnetic Remote Catheter Ablation, Circulation. 2004;109:1472-1475.*

(Continued)

*Primary Examiner* — Serkan Akar

(57) ABSTRACT

A system and method is described for a catheter guidance system which allows an operator to use a mapping catheter to specify tissue target locations for the automatic guidance of a second therapeutic catheter. The operator places a mapping catheter at a desired location, and commands the catheter guidance system by either selecting a point on that catheter or one of the catheter electrode electrocardiograms. The operator may target the selected dynamic location, or tissue contact beyond that location on a specific side of the mapping catheter.

4 Claims, 4 Drawing Sheets

(56) References Cited

U.S. PATENT DOCUMENTS

| | | |
|---|---|---|
| 3,746,937 A | 7/1973 | Koike |
| 3,961,632 A | 6/1976 | Moossun |
| 4,063,561 A | 12/1977 | McKenna |
| 4,071,042 A | 1/1978 | Lombard et al. |
| 4,096,862 A | 6/1978 | DeLuca |
| 4,162,679 A | 7/1979 | Reenstierna |
| 4,173,228 A | 11/1979 | Van Steenwyk et al. |
| 4,244,362 A | 1/1981 | Anderson |
| 4,249,536 A | 2/1981 | Vega |
| 4,270,252 A | 6/1981 | Harrison et al. |
| 4,292,961 A | 10/1981 | Kawashima |
| 4,354,501 A | 10/1982 | Colley et al. |
| 4,392,634 A | 7/1983 | Kita |
| 4,671,287 A | 6/1987 | Fiddian-Green |
| 4,727,344 A | 2/1988 | Koga et al. |
| 4,735,211 A | 4/1988 | Takasugi |
| 4,809,713 A | 3/1989 | Grayzel |
| 4,860,744 A | 8/1989 | Johnson et al. |
| 4,869,247 A | 9/1989 | Howard, III et al. |
| 4,870,306 A | 9/1989 | Petersen |
| 4,943,770 A | 7/1990 | Ashley-Rollman et al. |
| 4,984,581 A | 1/1991 | Stice |
| 4,985,015 A | 1/1991 | Obermann et al. |
| 5,031,634 A | 7/1991 | Simon |
| 5,063,935 A | 11/1991 | Gambale |
| 5,083,562 A | 1/1992 | de Coriolis et al. |
| 5,090,956 A | 2/1992 | McCoy |
| 5,125,888 A | 6/1992 | Howard et al. |
| 5,167,626 A | 12/1992 | Casper et al. |
| 5,209,234 A | 5/1993 | LaRocca |
| 5,226,847 A | 7/1993 | Thomas et al. |
| 5,249,163 A | 9/1993 | Erickson |
| 5,255,680 A | 10/1993 | Darrow et al. |
| 5,257,636 A | 11/1993 | White |
| 5,269,759 A | 12/1993 | Hernandez et al. |
| 5,353,807 A | 10/1994 | DeMarco |
| 5,377,678 A | 1/1995 | Dumoulin et al. |
| 5,396,902 A | 3/1995 | Brennen et al. |
| 5,421,338 A | 6/1995 | Crowley et al. |
| 5,462,054 A | 10/1995 | Rapoport et al. |
| 5,485,748 A | 1/1996 | Zeamer |
| 5,492,131 A | 2/1996 | Galel |
| 5,546,948 A | 8/1996 | Hamm et al. |
| 5,550,469 A | 8/1996 | Tanabe et al. |
| 5,558,091 A | 9/1996 | Acker et al. |
| 5,573,012 A | 11/1996 | McEwan |
| 5,588,442 A | 12/1996 | Scovil et al. |
| 5,624,430 A | 4/1997 | Eton et al. |
| 5,645,065 A | 7/1997 | Shapiro et al. |
| 5,650,725 A | 7/1997 | Powell et al. |
| 5,654,864 A | 8/1997 | Ritter et al. |
| 5,656,030 A | 8/1997 | Hunjan et al. |
| 5,681,260 A | 10/1997 | Ueda et al. |
| 5,683,384 A | 11/1997 | Gough et al. |
| 5,702,420 A | 12/1997 | Sterling et al. |
| 5,702,433 A | 12/1997 | Taylor et al. |
| 5,704,897 A | 1/1998 | Truppe |
| 5,709,661 A | 1/1998 | Van Egmond et al. |
| 5,711,299 A | 1/1998 | Manwaring et al. |
| 5,769,843 A | 6/1998 | Abela et al. |
| 5,775,322 A | 7/1998 | Silverstein et al. |
| 5,779,694 A | 7/1998 | Howard et al. |
| 5,808,665 A | 9/1998 | Green |
| 5,821,920 A | 10/1998 | Rosenberg et al. |
| 5,843,153 A | 12/1998 | Johnston et al. |
| 5,844,140 A | 12/1998 | Seale |
| 5,851,185 A | 12/1998 | Berns |
| 5,904,691 A | 5/1999 | Barnett et al. |
| 5,919,135 A | 7/1999 | Lemuelson |
| 5,931,818 A | 8/1999 | Werp et al. |
| 5,971,976 A | 10/1999 | Wang et al. |
| 6,014,580 A | 1/2000 | Blume et al. |
| 6,015,414 A | 1/2000 | Werp et al. |
| 6,038,488 A | 3/2000 | Barnes et al. |
| 6,073,043 A | 6/2000 | Schneider |
| 6,104,944 A | 8/2000 | Martinelli |
| 6,122,538 A | 9/2000 | Sliwa, Jr. et al. |
| 6,128,174 A | 10/2000 | Ritter et al. |
| 6,129,668 A | 10/2000 | Haynor et al. |
| 6,148,823 A | 11/2000 | Hastings |
| 6,152,933 A | 11/2000 | Werp et al. |
| 6,157,853 A | 12/2000 | Blume et al. |
| 6,200,312 B1 | 3/2001 | Zikorous et al. |
| 6,216,027 B1 | 4/2001 | Willis et al. |
| 6,233,476 B1 | 5/2001 | Strommer et al. |
| 6,241,671 B1 | 6/2001 | Ritter et al. |
| 6,292,678 B1 | 9/2001 | Hall et al. |
| 6,295,466 B1 | 9/2001 | Ishikawa et al. |
| 6,296,604 B1 | 10/2001 | Garibaldi et al. |
| 6,298,257 B1 | 10/2001 | Hall et al. |
| 6,304,768 B1 | 10/2001 | Blume et al. |
| 6,311,082 B1 | 10/2001 | Creighton, IV et al. |
| 6,314,312 B1 | 11/2001 | Wessels et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,381,485 B1 | 4/2002 | Hunter et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,454,776 B1 | 9/2002 | Tajima et al. |
| 6,459,924 B1 | 10/2002 | Creighton, IV et al. |
| 6,459,926 B1 | 10/2002 | Nowlin et al. |
| 6,475,223 B1 | 11/2002 | Werp et al. |
| 6,490,474 B1 | 12/2002 | Willis et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,529,761 B2 | 3/2003 | Creighton, IV et al. |
| 6,537,196 B1 | 3/2003 | Creighton, IV et al. |
| 6,562,019 B1 | 5/2003 | Sell |
| 6,575,977 B1 | 6/2003 | Michelson |
| 6,582,429 B2 | 6/2003 | Krishnan et al. |
| 6,587,709 B2 | 7/2003 | Solf et al. |
| 6,594,517 B1 | 7/2003 | Nevo |
| 6,630,879 B1 | 10/2003 | Creighton, IV et al. |
| 6,662,034 B2 | 12/2003 | Segner et al. |
| 6,667,660 B2 | 12/2003 | Schrodinger et al. |
| 6,669,693 B2 | 12/2003 | Friedman |
| 6,677,752 B1 | 1/2004 | Creighton, IV et al. |
| 6,692,492 B2 | 2/2004 | Simpson et al. |
| 6,702,804 B1 | 3/2004 | Ritter et al. |
| 6,704,694 B1 | 3/2004 | Basdogan et al. |
| 6,714,901 B1 | 3/2004 | Cotin et al. |
| 6,726,675 B1 | 4/2004 | Beyar |
| 6,733,511 B2 | 5/2004 | Hall et al. |
| 6,740,103 B2 | 5/2004 | Hall et al. |
| 6,752,767 B2 | 6/2004 | Turovskly et al. |
| 6,755,816 B2 | 6/2004 | Ritter et al. |
| 6,757,557 B1 | 6/2004 | Bladen et al. |
| 6,771,996 B2 | 8/2004 | Bowe et al. |
| 6,776,165 B2 | 8/2004 | Jin |
| 6,786,219 B2 | 9/2004 | Garibaldi et al. |
| 6,817,364 B2 | 11/2004 | Garibaldi et al. |
| 6,833,814 B2 | 12/2004 | Gilboa et al. |
| 6,834,201 B2 | 12/2004 | Gillies et al. |
| 6,853,965 B2 | 2/2005 | Massie et al. |
| 6,902,528 B1 | 6/2005 | Garibaldi et al. |
| 6,914,552 B1 | 7/2005 | McEwan |
| 6,950,689 B1 | 9/2005 | Willis et al. |
| 6,960,847 B2 | 11/2005 | Suzuki et al. |
| 6,961,632 B2 | 11/2005 | Hashimoto et al. |
| 6,970,733 B2 | 11/2005 | Willis et al. |
| 7,280,863 B2 | 10/2007 | Shachar |
| 7,282,034 B2 | 10/2007 | Burbank et al. |
| 7,316,700 B2 | 1/2008 | Alden et al. |
| 7,341,063 B2 | 3/2008 | Garibaldi et al. |
| 7,346,379 B2 | 3/2008 | Eng et al. |
| 7,468,042 B2 | 12/2008 | Turovskly et al. |
| 7,495,537 B2 | 2/2009 | Tunay |
| 7,543,239 B2 | 6/2009 | Viswanathan et al. |

(56) References Cited

U.S. PATENT DOCUMENTS

| | | |
|---|---|---|
| 7,660,023 B2 | 2/2010 | Hunter et al. |
| 7,725,157 B2 | 5/2010 | Dumoulin et al. |
| 7,751,867 B2 | 7/2010 | Viswanathan |
| 7,769,427 B2 | 8/2010 | Shachar |
| 7,840,253 B2 | 11/2010 | Tremblay et al. |
| 7,850,642 B2 | 12/2010 | Moll et al. |
| 7,869,854 B2 | 1/2011 | Shachar et al. |
| 7,873,402 B2 | 1/2011 | Shachar |
| 7,963,288 B2 | 6/2011 | Rosenberg et al. |
| 7,972,298 B2 | 7/2011 | Wallace et al. |
| 7,974,681 B2 | 7/2011 | Wallace et al. |
| 8,000,773 B2 | 8/2011 | Rousso et al. |
| 8,027,714 B2 | 9/2011 | Shachar |
| 8,041,413 B2 | 10/2011 | Barbagli et al. |
| 8,052,636 B2 | 11/2011 | Moll et al. |
| 2001/0004215 A1 | 6/2001 | Kubota et al. |
| 2001/0021805 A1 | 9/2001 | Blume et al. |
| 2002/0022777 A1 | 2/2002 | Creighton, IV et al. |
| 2002/0055674 A1 | 5/2002 | Ben-haim et al. |
| 2002/0058866 A1 | 5/2002 | Segner et al. |
| 2002/0058884 A1 | 5/2002 | Burbank et al. |
| 2002/0103430 A1 | 8/2002 | Hastings et al. |
| 2002/0168618 A1 | 11/2002 | Anderson et al. |
| 2002/0177765 A1 | 11/2002 | Bowe et al. |
| 2003/0014044 A1 | 1/2003 | Krishnan et al. |
| 2003/0036696 A1 | 2/2003 | Willis et al. |
| 2003/0065271 A1 | 4/2003 | Khoury |
| 2003/0082056 A1 | 5/2003 | Ohya et al. |
| 2003/0114727 A1 | 6/2003 | Wallace |
| 2003/0195433 A1 | 10/2003 | Turovskly et al. |
| 2003/0205941 A1 | 11/2003 | Suzuki et al. |
| 2003/0212373 A1 | 11/2003 | Hall et al. |
| 2003/0233112 A1 | 12/2003 | Alden et al. |
| 2004/0019447 A1 | 1/2004 | Shachar |
| 2004/0054279 A1 | 3/2004 | Hanley |
| 2004/0097805 A1 | 5/2004 | Verard et al. |
| 2004/0097806 A1 | 5/2004 | Hunter et al. |
| 2004/0097965 A1 | 5/2004 | Gardeski et al. |
| 2004/0199074 A1 | 10/2004 | Ritter et al. |
| 2004/0249262 A1 | 12/2004 | Werp et al. |
| 2004/0249263 A1 | 12/2004 | Creighton |
| 2004/0267156 A1 | 12/2004 | Turovskly et al. |
| 2005/0004449 A1 | 1/2005 | Mitschke et al. |
| 2005/0021078 A1 | 1/2005 | Vleugels et al. |
| 2005/0096589 A1 | 5/2005 | Shachar |
| 2005/0203375 A1 | 9/2005 | Wills et al. |
| 2005/0222554 A1 | 10/2005 | Wallace et al. |
| 2005/0256521 A1 | 11/2005 | Kozel |
| 2006/0058663 A1 | 3/2006 | Willis et al. |
| 2006/0095022 A1 | 5/2006 | Moll et al. |
| 2006/0114088 A1 | 6/2006 | Shachar |
| 2006/0116633 A1 | 6/2006 | Shachar |
| 2006/0116634 A1 | 6/2006 | Shachar |
| 2006/0150854 A1 | 7/2006 | Benninger et al. |
| 2006/0217697 A1 | 9/2006 | Lau et al. |
| 2006/0226713 A1 | 10/2006 | Lehr et al. |
| 2006/0270903 A1 | 11/2006 | Uchiyama et al. |
| 2006/0276775 A1 | 12/2006 | Rosenberg et al. |
| 2007/0016006 A1 | 1/2007 | Shachar |
| 2007/0016131 A1 | 1/2007 | Munger et al. |
| 2007/0043338 A1 | 2/2007 | Moll et al. |
| 2007/0062547 A1 | 3/2007 | Pappone |
| 2007/0066880 A1 | 3/2007 | Lee et al. |
| 2007/0083193 A1* | 4/2007 | Werneth ............... A61B 5/0422 606/41 |
| 2007/0118215 A1 | 5/2007 | Moaddeb |
| 2007/0197869 A1 | 8/2007 | Uchiyama et al. |
| 2007/0197872 A1 | 8/2007 | Uchiyama et al. |
| 2007/0197891 A1 | 8/2007 | Shachar |
| 2008/0027313 A1 | 1/2008 | Shachar |
| 2008/0039880 A1 | 2/2008 | Nohilly et al. |
| 2008/0058656 A1 | 3/2008 | Costello et al. |
| 2008/0091193 A1 | 4/2008 | Kauphusman et al. |
| 2008/0177139 A1 | 7/2008 | Courtney et al. |
| 2008/0230702 A1 | 9/2008 | Rousso et al. |
| 2008/0249395 A1 | 10/2008 | Shachar et al. |
| 2008/0297287 A1 | 12/2008 | Shachar et al. |
| 2009/0030411 A1 | 1/2009 | Werneth et al. |
| 2009/0078571 A1 | 3/2009 | Abarra et al. |
| 2009/0078875 A1 | 3/2009 | Rousso et al. |
| 2009/0209950 A1 | 8/2009 | Starksen |
| 2009/0231073 A1 | 9/2009 | Horisaka et al. |
| 2009/0248014 A1 | 10/2009 | Shachar et al. |
| 2009/0253985 A1 | 10/2009 | Shachar et al. |
| 2009/0275828 A1 | 11/2009 | Shachar et al. |
| 2010/0130854 A1 | 5/2010 | Shachar et al. |
| 2010/0152590 A1 | 6/2010 | Moore et al. |
| 2010/0256558 A1 | 10/2010 | Olson et al. |
| 2010/0305402 A1 | 12/2010 | Shachar et al. |
| 2010/0305429 A1 | 12/2010 | Shachar et al. |
| 2011/0178532 A1 | 7/2011 | Amiri et al. |
| 2011/0230896 A1 | 9/2011 | Wallace et al. |
| 2011/0238083 A1 | 9/2011 | Moll et al. |
| 2011/0301497 A1 | 12/2011 | Shachar et al. |
| 2011/0319715 A1 | 12/2011 | Uchiyama et al. |

FOREIGN PATENT DOCUMENTS

| | | |
|---|---|---|
| EP | 1 059 067 | 12/2000 |
| EP | 1 115 327 | 7/2001 |
| GB | 2367803 A | 4/2002 |
| JP | 2000-509316 | 7/2000 |
| JP | 2001-448 | 1/2001 |
| JP | 2001-509038 | 7/2001 |
| JP | 2001-514040 | 9/2001 |
| WO | WO 95-01757 A1 | 1/1995 |
| WO | WO 97-29803 A1 | 8/1997 |
| WO | WO 98-35720 A2 | 8/1998 |
| WO | WO 99-11189 A1 | 3/1999 |
| WO | WO 99-23934 A2 | 5/1999 |
| WO | WO 00-76141 A1 | 2/2000 |
| WO | WO 02-19908 A1 | 3/2002 |
| WO | WO 02-34131 A1 | 5/2002 |
| WO | WO 02-094115 A2 | 11/2002 |
| WO | WO 02-094115 A3 | 11/2002 |
| WO | WO 2004-006795 | 1/2004 |
| WO | WO 2005-042053 A2 | 5/2005 |
| WO | WO 2005-042053 A3 | 5/2005 |
| WO | WO 2005-112813 A1 | 12/2005 |
| WO | WO 2007-100559 A2 | 9/2007 |

OTHER PUBLICATIONS

Bergveld, Piet, "Development, Operation, and Application of the Ion-Sensitive Field-Effect Transistor as a Tool for Electrophysiology," IEEE Transactions on Biomedical Engineering, vol. BME-19, No. 5, Sep. 1972, 10 pages.

Canadian Office Action for Application No. 2542863, dated Sep. 30, 2010.

Extended European Search Report from 09005296.0, Aug. 19, 2009, 3 pages.

Faddis et al., "Novel, Magnetically Guided Catheter for Endocardial Mapping and Radiofrequency Catheter Ablation," Journal of the American Heart Association, Nov. 11, 2002.

Fink et al., "An Optically Switched PS-Radar for Pictorial Representation of Object Structures in Human Tissue," Experimentelle Technik Der Physik, vol. 38, No. 3, 1990, pp. 197-206, 10 pages.

International Search Report for PCT/US2010/036149, dated Sep. 29, 2010.

International Search Report for PCT/US2010/052684, dated Dec. 6, 2010.

International Search Report for PCT/US2010/052696, dated Dec. 8, 2010.

International Search Report from PCT/US03/22122, Nov. 6, 2003, 9 pages.

International Search Report from PCT/US2007/004416, Aug. 24, 2007, 5 pages.

International Search Report from PCT/US2008/056277, Nov. 18, 2008, 7 pages.

International Search Report from PCT/US2008/060525, Oct. 31, 2008, 6 pages.

(56) References Cited

OTHER PUBLICATIONS

International Search Report from PCT/US2009/039659, Jul. 6, 2009, 4 pages.
Ishiyama, K.; Sendoh, M.; Arai, K.I.; Magnetic micromachines for medical applications. Journal of Magnetism and Magnetic Materials. 2002; vol. 242; pp. 41-46.
Materials Library in FEMM 4.0, May 18, 2007, pp. 3-4.
Ritter, J.A.; Ebner, A.D.;Daniel, K.D.; Stewart, K.L.; Application of high gradient magnetic separation principles to magnetic drug targeting. Journal of Magnetism and Magnetic Materials. 2004; vol. 280; pp. 184-201.
Standard Specifications for Permanent Magnet Materials, Magnetic Materials Producers Association, 1964.
Supplementary Partial European Search Report from 04795885.5 Nov. 18, 2008, 5 pages.
Totsu, K.; Haga, Y.; Esashi, M.; Three-axis magneto-impedance effect sensor system for detecting position and orientation of catheter tip. Sensors and Actuators. 2004; Issue A 111; pp. 304-309.

* cited by examiner

SYSTEM AND METHOD FOR TARGETING CATHETER ELECTRODES

CROSS-REFERENCE TO RELATED APPLICATIONS

This application is a continuation of U.S. patent application Ser. No. 12/615,176, filed Nov. 9, 2009, the entirety of which is incorporated herein by reference and is to be considered part of this specification.

BACKGROUND

Field of the Invention

The invention relates to the systems and methods for guiding, steering and advancing an invasive medical device in a patient.

Description of the Related Art

In cardiac electrophysiological procedures, mapping catheters are used to define the geometry of a coronary chamber and map its surface electrocardiogram. Mapping catheters contain an array of electrodes which are used for position location and sensing the surface electrical activity. For sensing electrical activity, these electrodes are either used individually or in differential pairs, depending upon the type of sensory hardware available. When the surface has been fully mapped, a mapping catheter is often used in conjunction with an ablation catheter to locate and deliver therapeutic treatment at specific locations. The mapping catheter is returned to the area of interest, and the electrogram at each electrode or electrode pair is observed on the data recorder to determine the precise location along the mapping catheter for treatment. The ablation catheter is then guided independently to that location to deliver radiofrequency energy. Unfortunately, mapping of the heart chamber using prior art systems is a time-consuming process that increases the cost and risk of ablation procedures. The mapping process is complicated by the fact that the walls of a beating heart, not stationary, and the surgeon using traditional mapping catheters, does not have adequate control of the distal end of the catheter.

SUMMARY

The system and method described herein solve these and other problems by incorporating algorithms in a catheter guidance and control system that allows the operator to specify a target location as either a mapping catheter electrode, another location on the mapping catheter, or a mapping catheter electrode electrogram. The mapping process includes moving a catheter about a coronary chamber to define the average location of the walls and the electrical activity of the nerves within those walls during the heartbeat cycle.

The catheter guidance system then uses this live moving location to guide the therapeutic ablation catheter to this location or to tissue contact (e.g., where the tip of the catheter maintains relatively continuous contact with the surface of the heart chamber wall throughout the heartbeat cycle) near this location. This is done to increase the accuracy of targeting tissue contact at the location which is not possible with the targeting of a static geometric map. In one embodiment, the moving location corresponds to a Cartesian point on a geometric map which represents the average position of the tissue location that passes through that point.

In one embodiment, a spiral mapping catheter is manually positioned against the tissue surface. In one embodiment, a spiral mapping catheter includes a type of mapping catheter with a plurality of electrodes arranged along its coiled distal end. In one embodiment, the spiral mapping catheter can include five or more electrodes, ten or more electrodes, twenty or more electrodes, 50 or more electrodes, etc. In one embodiment, one or more of the electrodes involve a conductive ring on the catheter. The electrodes can be wired through the catheter line to the position detection and heart electrogram sensing hardware.

Manual controls are provided to adjust the amount of coil to make it larger or smaller, as well as to bend the assembly back and forth during the manual mapping process.

A magnetically-guided ablation catheter is introduced into the chamber to be used to deliver therapeutic energy. The an ablation catheter can be used in an ablation procedure to apply energy (e.g., radio frequency electrical) to a specific location within the heart is to necrotize (kill) tissue and block neural conduction pathways as to eliminate electrical signals that are the cause of cardiac arrhythmias. In a magnetic guidance system, a magnet (either a permanent magnet and/or an electromagnet) is provided to the distal end of the catheter and the distal end is then guided into position by a system of electromagnets external to the patient.

The catheter guidance control and imaging system is given the location of the distal electrode of the spiral mapping catheter as the desired position for the distal tip of the ablation catheter. The catheter guidance control and imaging system moves the ablation catheter distal tip into contact with the distal electrode of the spiral catheter. As the spiral catheter electrode moves, the catheter guidance system adjusts the ablation catheter location to maintain contact with that electrode.

In one embodiment, the catheter guidance control and imaging system moves the catheter tip into contact with the distal electrode of the spiral catheter and then moves the distal tip of the catheter past the spiral catheter electrode until continuous contact is made between the catheter tip and the chamber wall.

In one embodiment, the operator selects the target electrode on the spiral catheter by positioning the mouse cursor over the electrode and double-clicking the left mouse button. The catheter guidance and control system continuously sends this electrode's live position as a target position for automatic guidance to automatically advance, steer and/or push a catheter toward a desired position.

In one embodiment, the operator selects the target electrode on the spiral catheter by positioning the mouse cursor over the electrode's electrogram trace and double-clicking the left mouse button. The associated electrode's live position is used as target for automatic guidance.

In one embodiment, the operator selects a target electrode pair on the spiral catheter by selecting the electrode pair's electrogram trace. The catheter guidance and control system continuously sends the average position of the electrode pair as the desired position.

In one embodiment, the operator selects a location between electrodes by positioning the mouse cursor over a location on the mapping catheter and double-clicking the mouse button. The catheter guidance and control system continuously sends an interpolated position between the adjacent electrode pairs as the desired position.

In one embodiment, the operator may target tissue contact on a specific side of a mapping catheter by selecting a side preference cursor which appears when the mouse cursor is in close proximity to the mapping catheter.

In one embodiment, catheter guidance includes introducing a mapping catheter into a patient, moving the mapping catheter within the patient to bring an electrode provided to the mapping catheter in contact with tissues at various locations to generate a desired map, identifying a target location from the map and placing an electrode of the mapping catheter proximate to the target location, introducing a therapeutic catheter into the patient and guiding the therapeutic catheter to a location of the electrode. In one embodiment, the therapeutic catheter is moved past the location of the electrode. In one embodiment, the mapping catheter is guided using magnetic fields. In one embodiment, the therapeutic catheter is guided using magnetic fields.

One embodiment includes a system for catheter guidance having a mapping catheter having at least one electrode proximate to a distal end of the mapping catheter, therapeutic catheter, a first catheter guidance and control system that moves the mapping catheter to bring the at least one electrode in contact with tissues at various locations to generate a desired map, and a second catheter guidance and control system that moves a distal end portion of the therapeutic catheter to a location of the at least one electrode. In one embodiment, the therapeutic catheter includes an ablation catheter. In one embodiment, the second catheter guidance and control system includes a magnetic guidance and control system that uses a plurality of electromagnets to control a position of a magnet provided to a distal end of the therapeutic catheter. In one embodiment, the first catheter guidance and control system comprises a magnetic guidance and control system that uses a plurality of electromagnets to control a position of a magnet provided to a distal end of the mapping catheter. In one embodiment, the second catheter guidance and control system automatically moves a distal end portion of the therapeutic catheter to a location of the at least one electrode

DETAILED DESCRIPTION

Figure 1:
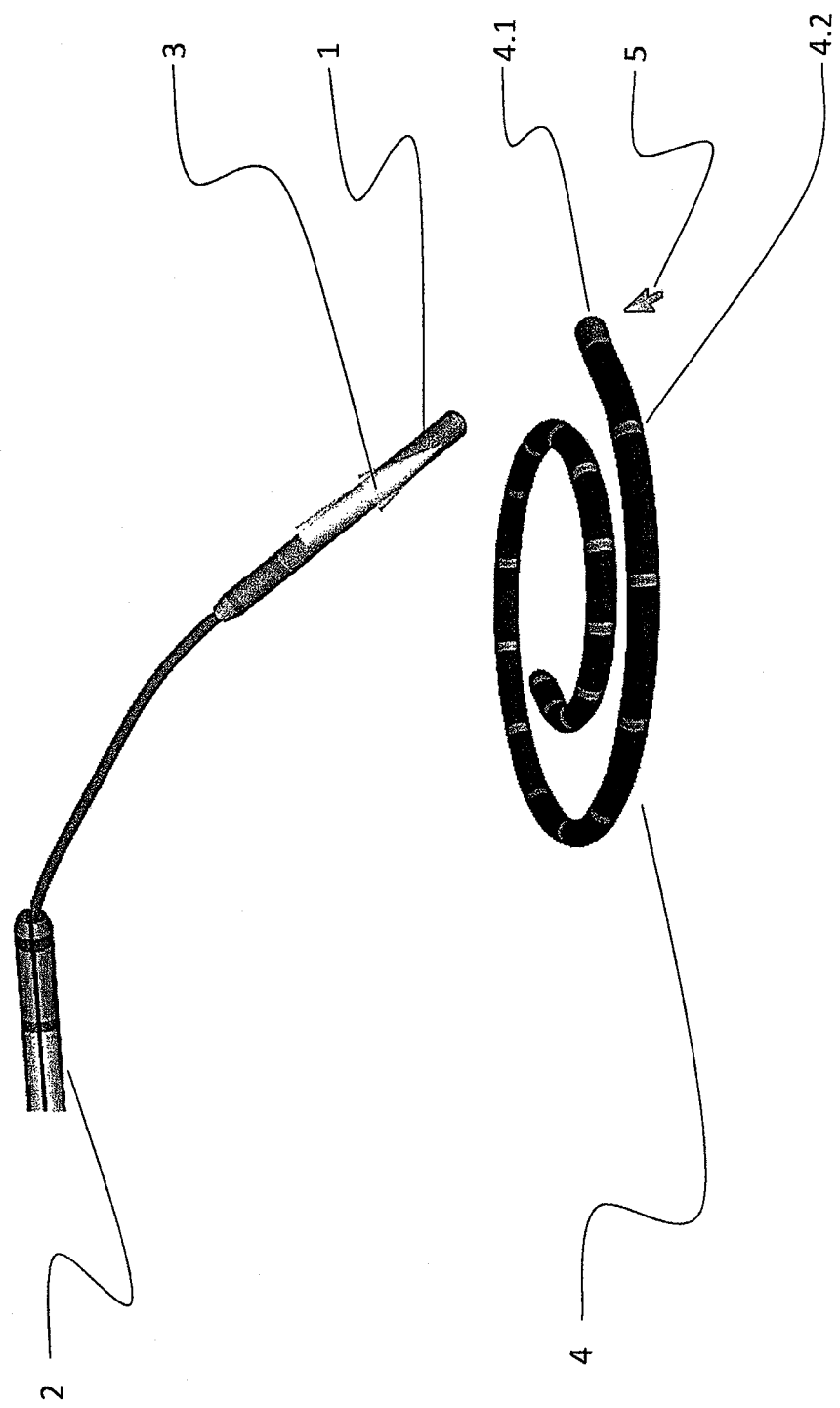
FIG. 1 is an illustration of an ablation catheter, spiral catheter and the catheter guidance and control elements.

FIG. 1 shows a distal end of a spiral mapping catheter 4 and a distal end of an ablation catheter 1. The mapping catheter 4 includes a plurality of electrodes including an electrode 4.1 disposed at or near the distal end of the catheter 4, an electrode 4.2 disposed at a position on the catheter 4 less distal than the electrode 4.1, etc. The ablation catheter 1 is introduced into a coronary chamber via a sheath (or introducer) 2. The sheath (or introducer) 2 includes a tube which is inserted through a vein or other pathway or orifice into the heart. Catheters, wires and/or fluids can be introduced into the heart chamber through this tube.

In one embodiment, the tip of the ablation catheter 1 contains a magnetically-doped core element and sensory electrodes. The magnetic indicator 3 displays the current direction of the magnetic field that is guiding the catheter tip.

A spiral mapping catheter 4 is introduced into the chamber and manually guided by levers on its handle (e.g., at the proximal end, not shown) to a desired location. The operator uses a mouse cursor 5 to double-click on a representation of the distal electrode 4.1 of the spiral catheter 4 to command the catheter guidance control and imaging system to guide the ablation catheter 1 to the spiral catheter electrode 4.1. The operator may also select any location between locations, such as between the distal 4.1 and second electrode 4.2 and a linearly interpolated position will be sent to the catheter guidance control and imaging system.

Figure 2:
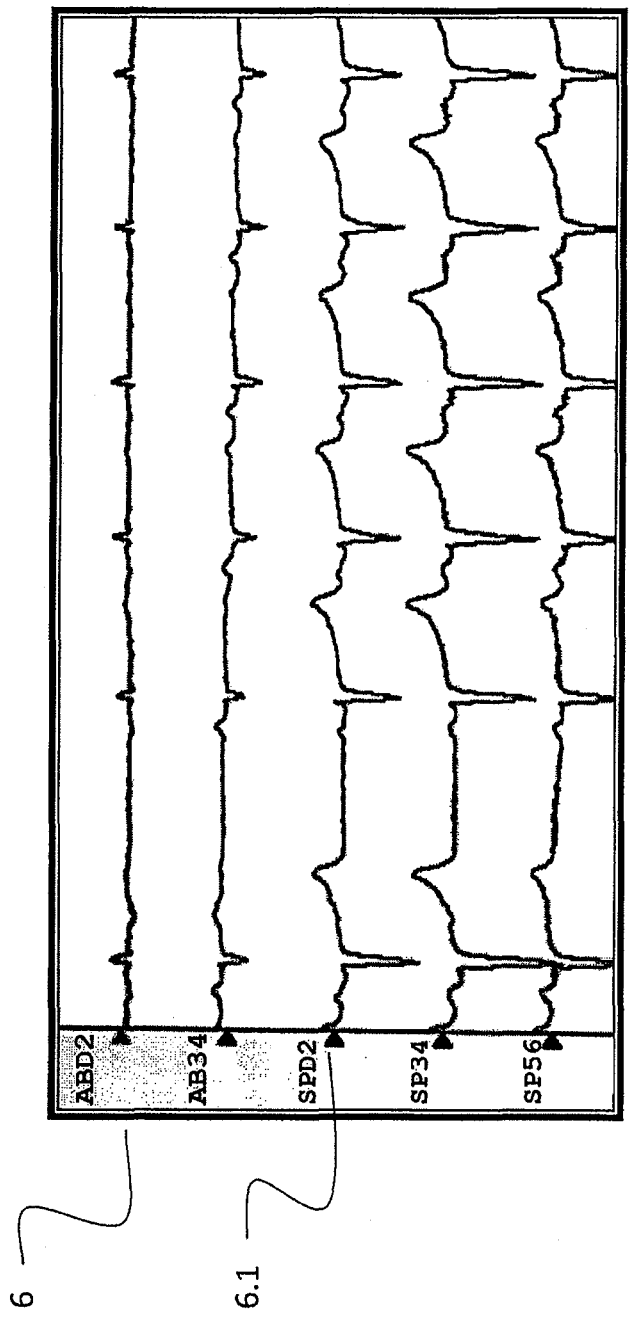
FIG. 2 is an illustration of a set of catheter electrode electrogram traces.

FIG. 2 is an illustration of a set of catheter electrode electrogram traces 6. In one embodiment, the electrogram configured as a time versus amplitude plot of the electrical potential as measured at a specific point on, or in the body. Electrograms for each electrode pair can be displayed on the mapping system and/or on a separate ECG system.

Alternately to the process described in FIG. 1, the operator can use the mouse to double-click on a spiral mapping catheter's electrogram trace to command the catheter guidance, control and imaging system to guide the ablation catheter to that spiral catheter electrode or electrode pair. In this alternate embodiment, the operator selects the distal pair of spiral catheter electrodes 6.1 and the ablation catheter is guided to an average location between the distal electrode 4.1 and second electrode 4.2.

Figure 3:
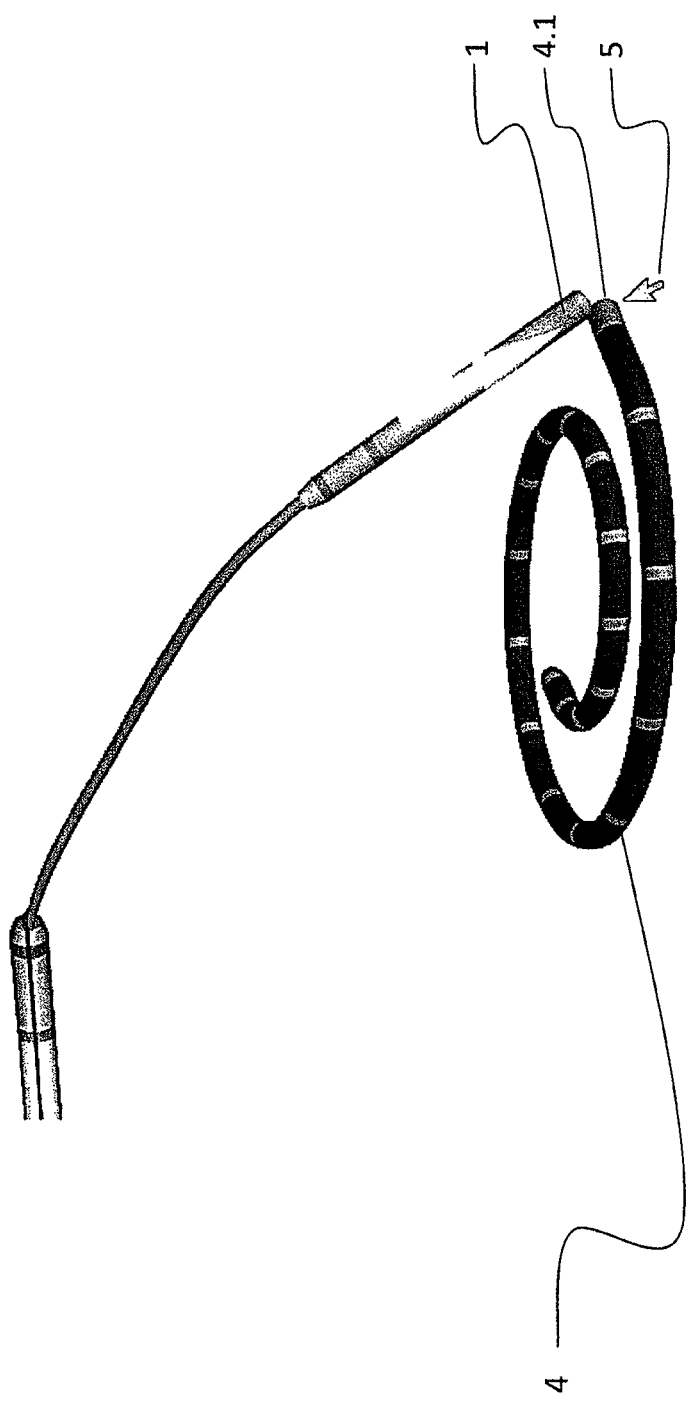
FIG. 3 is an illustration of an ablation catheter in contact with a spiral catheter electrode.

FIG. 3 shows the ablation catheter 1 in contact with a spiral catheter electrode where the ablation catheter 1 has been guided into contact with the spiral mapping catheter's distal electrode 4.1. The live electrode position of the catheter tip and the live electrode position of the distal spiral catheter electrode can be continuously synchronized by the catheter guidance and control system.

Figure 4:
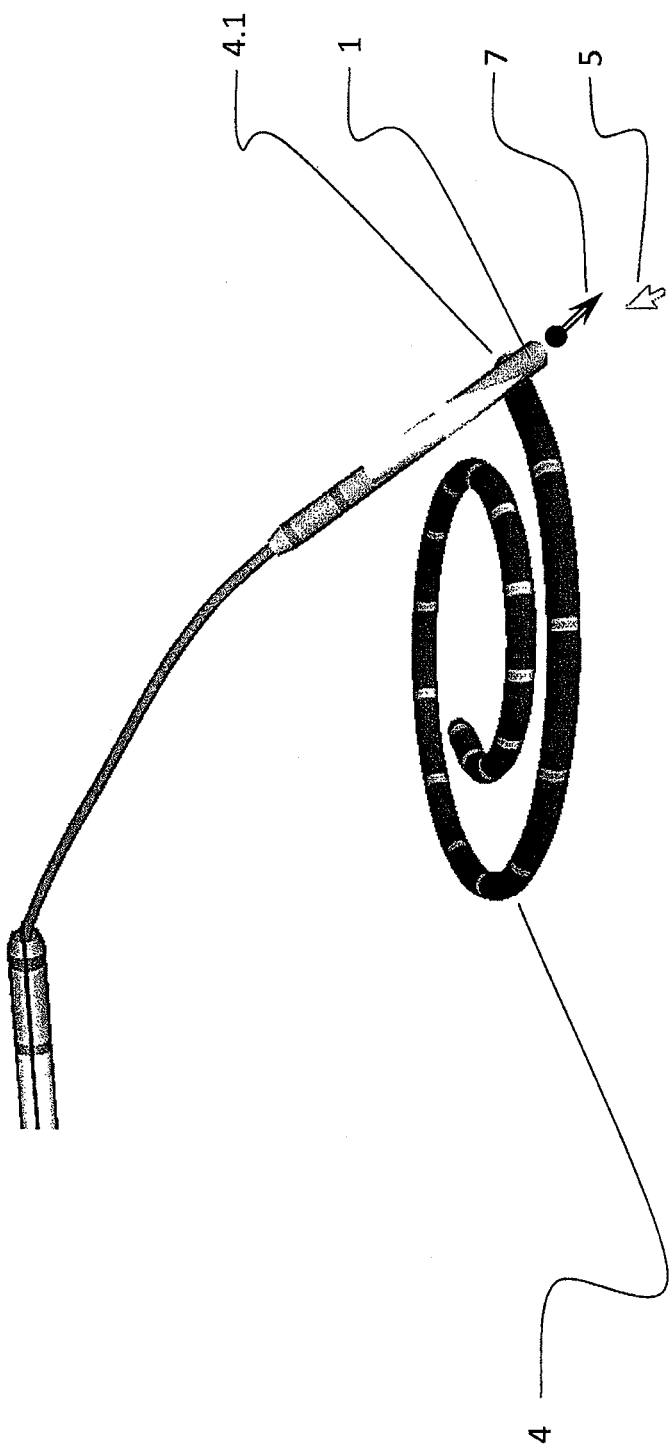
FIG. 4 is an illustration of an ablation catheter tip moving beyond a spiral catheter electrode in order to acquire tissue contact near that electrode.

FIG. 4 shows the ablation catheter 1 moving beyond the spiral catheter electrode 4.1 in order to acquire tissue contact near that electrode. The operator has elected to automatically guide the ablation catheter 1 past the spiral catheter distal electrode 4.1 until tissue contact is made on the outside of the spiral catheter 4. The operator has used the side preference cursor 7 to select the side preference which moved the desired position that side of the spiral catheter electrode 4.1.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The claims are thus to be understood to include what is specifically illustrated and described above, what is conceptually equivalent, what can be obviously substituted and also what essentially incorporates the essential idea of the invention.

It is to be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but can be used alone or combined in other combinations. The excision of any disclosed element of the invention is explicitly contemplated as within the scope of the invention.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the invention is limited only by the claims.

What is claimed is:

1. A method for catheter guidance in a heart, comprising:
    introducing a spiral mapping catheter into a patient, said mapping catheter further comprising a coiled distal end and a plurality of electrodes are arranged along said coiled distal end to form a conductive ring;
    moving said mapping catheter within the patient to bring one or more of said plurality of electrodes of said mapping catheter in contact with tissues in the heart at various locations to generate a desired map;
    identifying a target location from said map and placing one or more of said plurality of electrodes of said mapping catheter proximate to said target location;
    displaying at least one electrogram trace for said one or more of said plurality of electrodes;
    receiving an input that selects said target location with a cursor placed on said at least one electrogram trace for said one or more plurality of electrodes;
    synchronizing live electrode positions of the catheter tip and live electrode positions of the spiral catheter electrode;
    automatically guiding an ablation catheter to the one or more of said plurality of electrodes of said mapping catheter proximate to said target location in response to the received said input; and
    acquiring tissue contact between the tip of said ablation catheter and said target location by moving the tip of said ablation catheter past the one or more of said plurality of electrodes of said mapping catheter proximate to said target location.

2. The method of claim 1, further comprising bringing at least one pair of said plurality of electrodes of said mapping catheter in contact with tissues at various locations to generate said desired map.

3. The method of claim 2, wherein said at least one electrogram trace is for said at least one pair of said plurality of electrodes.

4. The method of claim 3, further comprising receiving said input that selects said target location with a cursor placed over said display of said electrogram trace for said at least one pair of said plurality of electrodes.

\* \* \* \* \*